United States Patent [19]

Slocum

[11] Patent Number: 4,677,973

[45] Date of Patent: Jul. 7, 1987

[54] PROXIMAL, TIBIAL OSTEOTOMY FOR LEVELING A TIBIAL PLATEAU

[76] Inventor: Barclay Slocum, 241 Sly Glass Dr., Eugene, Oreg. 97401

[21] Appl. No.: 737,737

[22] Filed: May 28, 1985

[51] Int. Cl.[4] .............................................. A61F 5/04
[52] U.S. Cl. ............................................... 128/92 VW
[58] Field of Search .............. 128/92 E, 92 EB, 92 H, 128/92 VW, 92 VK, 92 VY

[56] References Cited

U.S. PATENT DOCUMENTS

| | | | | |
|---|---|---|---|---|
| 4,409,973 | 10/1983 | Neufeld | .............................. | 128/92 E |
| 4,421,112 | 12/1983 | Mains et al. | ........................ | 128/92 E |
| 4,501,268 | 2/1985 | Comparetto | ....................... | 128/92 E |
| 4,502,474 | 3/1985 | Comparetto | ....................... | 128/92 E |

Primary Examiner—C. Fred Rosenbaum
Assistant Examiner—C. W. Shedd
Attorney, Agent, or Firm—Kolisch, Hartwell & Dickinson

[57] ABSTRACT

A method of performing a proximal tibial osteotomy, portion of the metaphysis of the tibia is cut free from a remaining (lower) portion of the tibia with a cylindrical cut which has a curvature axis that is perpendicular to the sagittal plane. The thus-cut proximal portion is rotated relative to the lower portion of the tibia to establish a new desired angular relation therebetween, and the two portions are then fixed relative to one another in any suitable manner, as by pinning.

2 Claims, 3 Drawing Figures

PROXIMAL, TIBIAL OSTEOTOMY FOR LEVELING A TIBIAL PLATEAU

BACKGROUND AND SUMMARY OF THE INVENTIONS

This invention relates generally to an osteotomy technique, and more particularly to a method for performing a greatly simplified proximal tibial osteotomy. A preferred manner of practicing the invention is described in conjunction with veterinary surgery on the leg of a dog.

The cranial or anterior cruciate ligament restrains cranial drawer or sliding motion of the tibia of a dog. When the cranial cruciate ligament is disrupted or injured, the tibia moves forward relative to the femur, leading to further injury of the musculature, ligaments or meniscus. A wide variety of methods of repairing the cranial cruciate ligament have been suggested, ranging from collagen ligament implants to synthetic ligament implants. Extra-articular repair devices have also been proposed, but none of these has been very successful. Collagen implants stretch with use, leaving the knee area unstable, while synthetic implants are unable to withstand the varied forces exerted on the knee. Extra-articular repairs decrease mobility, and place undue stress on the soft tissue surrounding the joint which is not designed for constant loads.

It has been recognized that one problem with most techniques for repairing a dog's cranial cruciate ligament is that the phenomenon of cranial tibial thrust has not been appreciated. This phenomenon results in force factors having compressive and cranial or anterior components. The compressive components are satisfactorily absorbed by the tibia, as are the cranial tibial forces when the cranial cruciate ligament is operating satisfactorily. When the cranial cruciate ligament is weakened by injury or is congenitally malformed, cranial tibial thrust can be a problem. Many prior efforts at repair of a weakened cranial cruciate ligament ignore the cranial tibial thrust phenomenon, and have failed to recognize that this phenomenon results in the ligament being placed under stress while healing was intended to occur. Such stress clearly retards or prevents healing.

Once cranial cruciate rupture occurs, so-called cranial drawer or sliding motion, that is, unrestrained cranial motion of the tibia with respect to the femur following such rupture, results in more severe injury to the dog's leg in the form of soft tissue (medial meniscus) impingement. Surgical attempts have been addressed to restraining cranial draw motion but, until recently, no attempt has been made to deal with internally generated cranial tibial thrust.

One technique which has been proposed over the years to deal with these problems is so-called cuneiform osteotomy—that is, surgical removal of a bone wedge to correct impairments to the bone, the musculature or the ligamental support structure associated therewith. For example, I describe such a technique in my now-pending, prior-filed patent application, Ser. No. 570,458, filed Jan. 12, 1984 for "APPARATUS AND METHOD FOR PERFORMING CUNEIFORM OSTEOTOMY".

According to that technique, and through the use of a saw-guide jig, two cuts are performed to remove a defined-angle wedge from the upper portion of a tibia. This cut wedge is removed, and the remaining tibial portions are rotated relative to one another and fixed in any suitable manner against further relative movement The method of the present invention proposes an improvement of that technique in the form of a great simplification.

A principal object of the invention is, therefore, to provide such a simplified osteotomy technique which offers a number of important procedural advantages.

According to a preferred method of practicing the invention, a curvilinear cut, and preferably a cut which is substantially cylindrical, is made in the proximal tibia about an axis which is substantially normal to the sagittal plane. This cut frees a caudal, tibial portion within the metaphyseal region from the remaining portion of the tibia that includes the diaphysis and the tibial crest. The thus-cut tibial portions are then rotated relative to one another by the desired corrective angle, without any translation (lateral offsetting) occurring between the metaphysis and the diaphysis, and fixed in any suitable manner against further relative movement, as by means of pins.

Among the important advantages offered by this technique are that (a) only a single cut in the tibia need be made during a surgical procedure, and that (b) this single cut allows infinitely adjustable relative rotation between the cut tibial portions to achieve any desired corrective angle, and that (c) the metaphyseal bone is better for healing.

These and other advantages and features of the invention will become more fully apparent when the description of the same below is read in conjunction with the accompanying drawings.

DETAILED DESCRIPTION OF THE INVENTION

Figure 1:
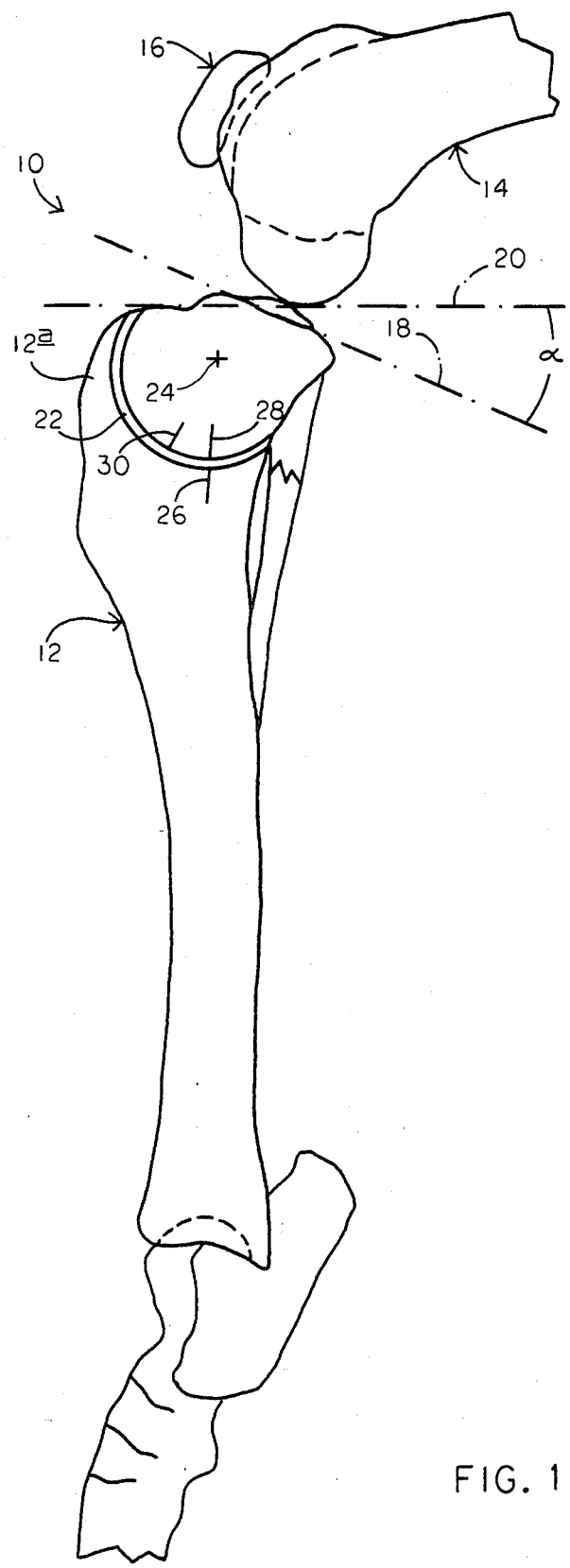
FIG. 1 is a fragmentary side-elevation showing a canine femoro tibial joint region at an early stage during performance of the invention, and particularly, just following that stage during which a curvilinear cut has been formed in the proximal end of the tibia.

Turning attention first to FIG. 1, indicated generally at 10 is the tibia-femur joint region in the leg of a dog. At 12 is the tibia, at 14 the femur, and at 16 the patella.

Dash-dot line 18 indicates the plane of the tibial plateau upon which femur 14 rests. Because, as can be seen, this plane is inclined with respect to a line perpendicular to a line between the center of motion in the stifle (knee) and hock (ankle), a cranial force, i.e., one to the left in FIG. 1, is exerted on tibia 12. This force is opposed by the cranial crutiate ligament, and contributes to the ligament's rupture. In addition, it prevents or at least inhibits, dramatically, healing of a ruptured ligament or its surgical replacement.

The main thrust of the present invention, in an ultimate sense, is to alter the angle of this plateau more toward the horizontal, such as that indicated by dash-dot line 20.

According to a preferred manner of practicing the invention, a curvilinear cut, and preferably what might be thought of as a cylindrical cut, 22 is performed in the proximal region 12a of the tibia, about an axis 24 which is substantially perpendicular to the sagittal plane—a plane parallel to the plane of FIG. 1. As can be appreciated, this single curved cut now permits relative rotation of the two thus cut-separated bone portions about axis 24 to an infinite number of different, preselected, corrected angles. In the particular illustration now being described, the desired corrective angle is indicated at $\alpha$, and typically is about 22.5-degrees.

Following the cutting operation, typically, a first pair of aligned linear marks 26, 28, which extend radially relative to axis 24, are prepared on the cut bone parts as shown. Another mark 30 is prepared on the cut (smaller) proximal bone part at an angle (to the left in FIG. 1) of relative to mark 28. Mark 30 is also radial relative to axis 24.

Figure 2:
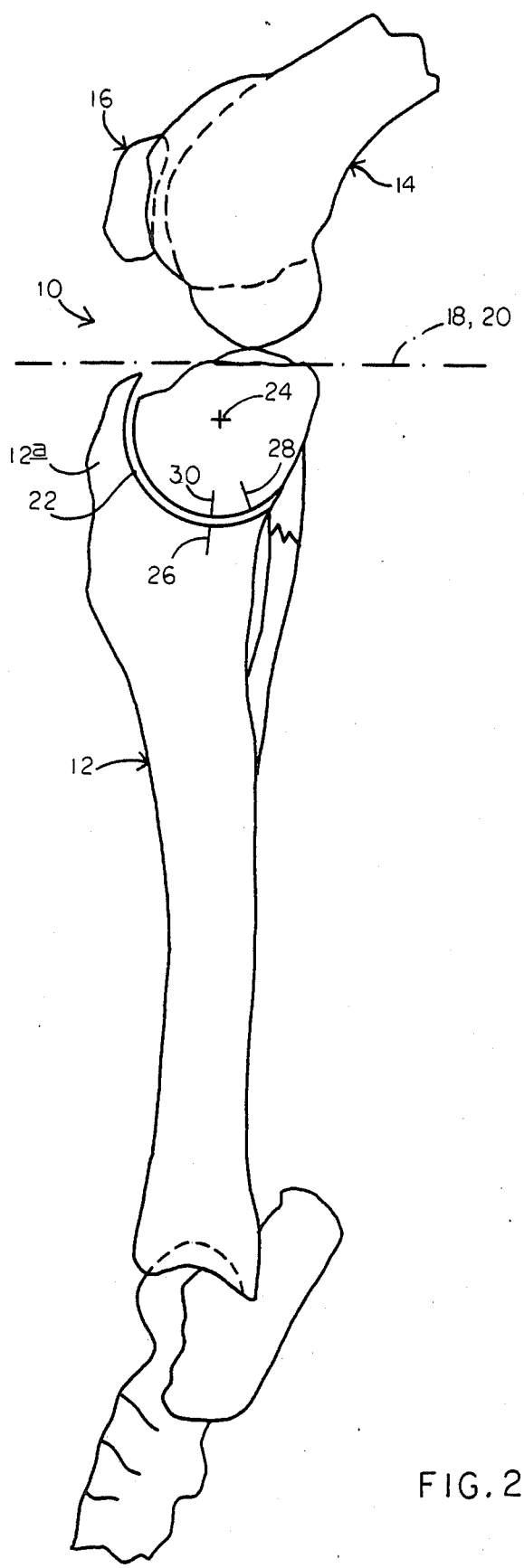
FIG. 2 is similar to FIG. 1, except that it shows a slightly later stage in the performance of the invention when the cut/separated tibial portions have been rotated relative to one another to correct the angle of the tibial plateau.

Switching attention now to FIG. 2, this illustrates the next stage in the procedure, in which the upper cut tibial bone portion is rotated about axis 24 an angle $\alpha$, to produce alignment between marks 26, 30 as shown. With this rotation accomplished, tibial plateau 18 and the horizontal 20 are substantially co-planar.

Figure 3:
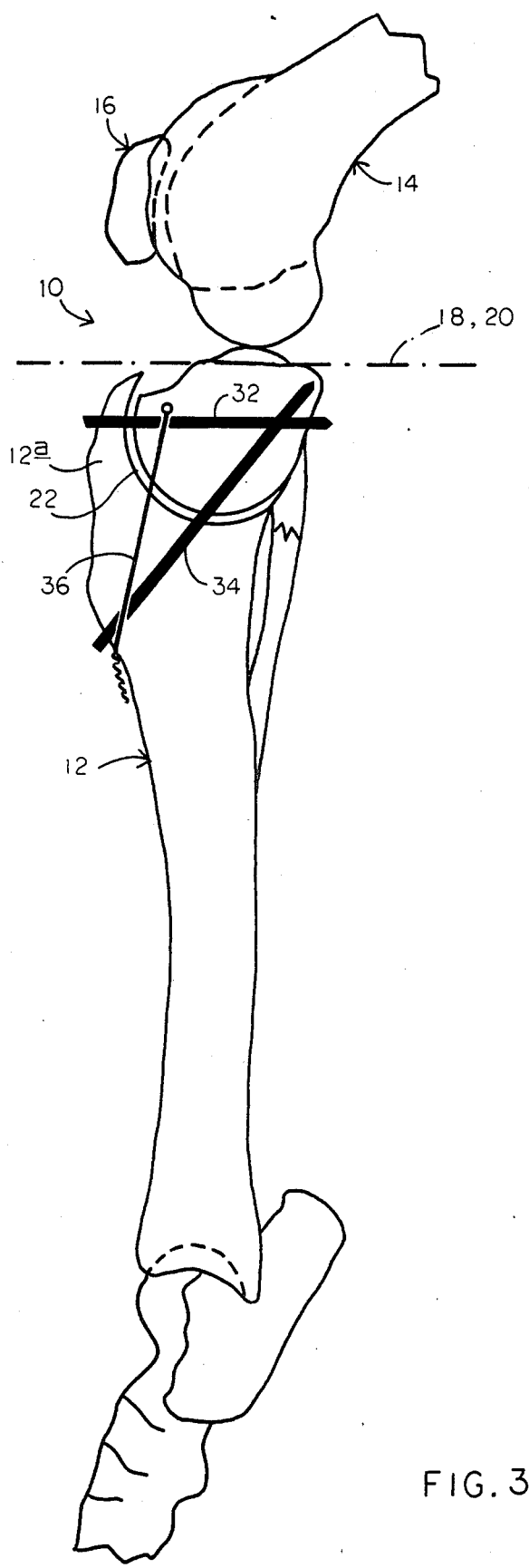
FIG. 3 is similar to FIG. 2 except that it shows a final stage in the procedure of the invention in which the rotated tibial bone portions have been fixed against further relative movement.

Finally addressing FIG. 3, this illustrates the final stage in the procedure in which the now-cut and rotated tibial bone portions are fixed against further relative movement, as by means of conventional Steinmann pins 32, 34, and a wire 36.

The advantages offered by the invention should now be apparent to those skilled in this art. Only a single cut, curvilinear and preferably cylindrical, is required to prepare the proximal portion of a tibia for relative rotation to correct the angular position of the tibial plateau. This single cut enables relative rotation to any desired angle, with infinite relative adjustments permitted. The single curvilinear cut proposed is an important step in practicing the invention. Obviously, it greatly simplifies a proximal tibial osteotomy.

Fixing of the cut/rotated bone portions can be accomplished, of course, in a variety of well-known ways.

Accordingly, while a preferred method of practicing the invention has been described herein, it is appreciated that variations and modifications are possible which come within the scope of the invention.

It is claimed and desired to secure by Letters Patent:

1. A method of performing a proximal tibial osteotomy comprising
    producing a curvilinear cut adjacent the proximal metaphysis of the tibia, the lower part of which cut is concave as viewed from such metaphysis, such cut being made generally perpendicular to the sagittal plane, to free a caudal, tibial portion within the metaphyseal region of the tibia for movement relative to the remaining portion of the tibia that includes the diaphysis of the tibia and the tibial crest,
    rotating the two thus-cut-separated tibial portions to produce a new angular relationship therebetween in such plane without effecting translation of the thus-cut-separated tibial portions relative to one another, and
    fixing the two thus-rotated portions to anchor them in such new angular relationship.

2. The method of claim 1, wherein production of a curvilinear cut is accomplished, more specifically, by generating a cylindrical cut.

* * * * *